(12) United States Patent
Kukuk

(10) Patent No.: US 7,179,220 B2
(45) Date of Patent: Feb. 20, 2007

(54) METHOD FOR GUIDING FLEXIBLE INSTRUMENT PROCEDURES

(75) Inventor: Markus Kukuk, Princeton, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 10/072,574

(22) Filed: Feb. 6, 2002

(65) Prior Publication Data

US 2002/0133057 A1    Sep. 19, 2002

Related U.S. Application Data

(60) Provisional application No. 60/266,954, filed on Feb. 7, 2001.

(51) Int. Cl.
*A61B 1/00* (2006.01)

(52) U.S. Cl. .................................................... 600/101

(58) Field of Classification Search ............... 600/101, 600/102, 145, 407; 606/1, 130; 703/2
See application file for complete search history.

(56) References Cited

U.S. PATENT DOCUMENTS

| | | | |
|---|---|---|---|
| 5,482,029 A * | 1/1996 | Sekiguchi et al. ........... | 600/109 |
| 6,409,686 B1 * | 6/2002 | Guthrie et al. .............. | 600/587 |
| 6,505,065 B1 * | 1/2003 | Yanof et al. ................. | 600/427 |
| 6,645,196 B1 * | 11/2003 | Nixon et al. .................... | 606/1 |
| 2001/0034530 A1* | 10/2001 | Malackowski et al. ...... | 606/130 |
| 2003/0149351 A1* | 8/2003 | Nowinski et al. ........... | 600/407 |
| 2003/0173113 A1* | 9/2003 | Alft et al. ...................... | 175/45 |
| 2003/0187351 A1* | 10/2003 | Franck et al. ................ | 600/429 |

OTHER PUBLICATIONS

Bricault, Ivan, et al., *Multi-Level Strategy for Computer-Assisted Transbronchial Biopsy*, MICCAI, 1998, LNCS 1496.
Geiger, Bernhard, *Real-Time Collision Detection and Response for Complex Environments*, IEEE, 2000, pp. 105-113.
Kukuk, Markus, *Registration of Real and Virtual Endoscopy—A Model and Image Based Approach*, Medicine Meets Virtual Reality, 8th Annual Conference, Jan. 2000.
Mori, Kensaku, et al., *A Method for Tracking Camera Motion of Real Endoscope by Using Virtual Endoscopy System*, Proc. Of SPIE, (2000), pp. 1-12.
Shannon, John J., et al., *Endobronchial Ultrasound-Guided Needle Aspiration of Mediastinal Adenopathy*, American Journal of Respiratory and Critical Care Medicine, vol. 153, 1996, pp. 1424-1430.
Sherbondy, Anthony J., et al., *Virtual Bronchoscopic Approach for Combining 3D CT and Endoscopic Video*, Proc. Of SPIE, vol. 3978, Feb. 2000, pp. 104-116.
Solomon, Stephen B., et al., *Real-Time Bronchoscope Tip Localization Enables Three-Dimensional CT Image Guidance for Transbronchial Needle Aspiration in Swine*, Chest, vol. 114, No. 5, 1998, pp. 1405-1410.
Wang, Ko-Pen, *Staging of Bronchogenic Carcinoma by Bronchoscopy*, Chest, 1994, 106:588-93.
White, Charles S., et al., *CT-Assisted Transbronchial Needle Aspiration: Usefulness of CT Fluoroscopy*, AJR, vol. 169, Aug., 1997.

* cited by examiner

*Primary Examiner*—John P. Leubecker
(74) *Attorney, Agent, or Firm*—Donald B. Paschburg; F. Chau & Associates LL

(57) ABSTRACT

A method for determining instructions for handling a flexible instrument comprises parameterizing the flexible instrument according to a plurality of parameters for handling the instrument, determining at least one instrument configuration, wherein the configuration describes at least one parameter, and determining instructions for handling the instrument according to the configuration.

15 Claims, 4 Drawing Sheets

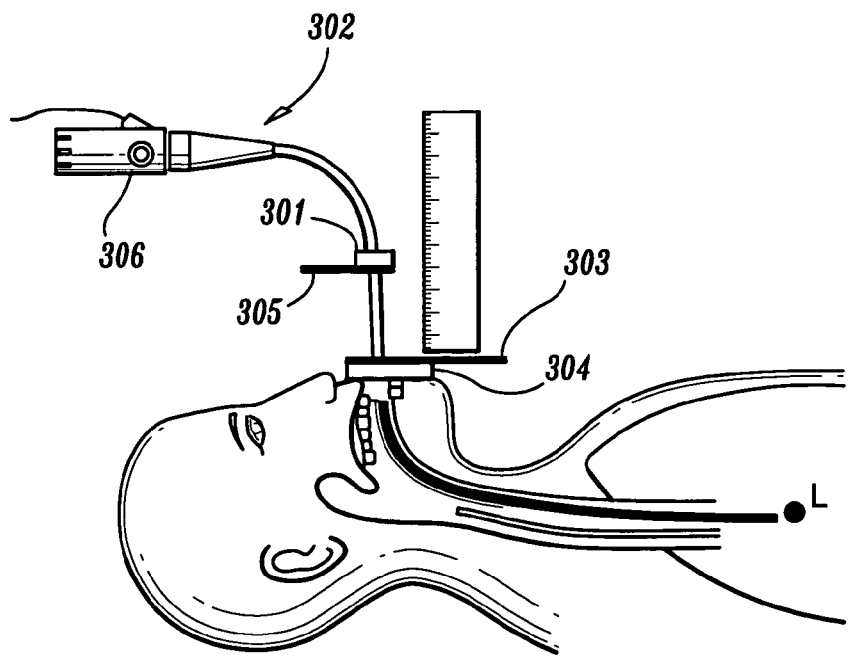

FIG. 3

1. Touch carina with the bronchoscope tip.
2. Move stopper to mouth-piece.
3. Withdraw bronchoscope 30 mm.
4. Rotate shaft until carina appears vertically in the bronchoscope's view.
5. Move stopper to mouth-piece and set its rotation-pointer to 0 degrees.

| 6. Move stopper $l$ mm away from mouth-piece and lock stopper. | 6. Withdraw bronchoscope $l$ mm. |
|---|---|
| 7. Insert bronchoscope into branch of the biopsy-site B until stopper hits the mouth-piece. | 7. Move stopper back to mouth-piece and lock stopper. |

8. Rotate endoscope shaft until the shaft rotation-pointer points to $\alpha$ degrees.
9. Set rotation of the bending-wheel to $\beta$ degrees.
10. Insert needle $d$ mm beyond the working channel outlet.

FIG. 4

METHOD FOR GUIDING FLEXIBLE INSTRUMENT PROCEDURES

CROSS-REFERENCE TO RELATED APPLICATIONS

This is a non-provisional application claiming the benefit of provisional application Ser. No. 60/266,954, filed on Feb. 7, 2001, the disclosure of which is incorporated herein by reference.

BACKGROUND OF THE INVENTION

1. Field of the Invention

The present invention relates to guiding endoscopic procedures, and more particularly to guiding a flexible instrument.

2. Discussion of Related Art

Transbronchial needle aspiration (TBNA) is a valuable minimally invasive procedure in the bronchoscopic diagnosis and staging of patients with lung cancer. The procedure allows nonsurgical access to lymph nodes from the inside of the tracheobronchial tree. Typically, a biopsy can be performed by maneuvering a bronchoscope to a desired site within the tracheobronchial tree. The surgeon can insert a tool, for example, a needle, through the bronchoscope and puncture the bronchial wall to hit a target behind, e.g., a tumor. This is literally a "blind" puncture since the target object is at no time visible through the bronchoscope. To increase the chance of hitting the target, a surgeon may take more than one tissue sample for every biopsy. Studies have shown that up to eight needle aspirations in the same site can be safely performed. However, there is no strategy for placing the aspirations other then a trial-and-error approach.

Despite the fact that the surgeon can perform more than one needle aspiration in a single biopsy, this procedure has a failure rate of about 60 to 80%, if the bronchial wall is not yet affected. The blind nature of the procedure and the physician's lack of confidence about where to position the needle are obstacles to the widespread use and positive diagnostic yield of TBNA. Performing a TBNA can include three-dimensional (3D) imagination (coordination of the learned three dimensional anatomy with a fish-eye distorted 2D video image) together with the handling of the endoscope (hand-eye-coordination).

Techniques used to guide TBNA can be classified into three different groups: imaging based technology, on-line visualization of the target and tracking of the bronchoscope.

Imaging based techniques can include, for example, fluoroscopy, CT and CT fluoroscopy. These techniques can show the endoscope, the advanced needle and the target lesion. Fluoroscopy produces a real-time two-dimensional image projection with poor contrast. Typically, the target lesion is not visible. Conventional CT produces images of adequate quality but the procedure can be cumbersome and time consuming since real-time imaging may not be possible and each sequence needs to be prescribed in advance. CT fluoroscopy is a term for continuous-imaging CT that allows the visualization of dynamic processes in real-time, like the insertion of a needle into the target lesion. However, this technique is limited to axial images and may need significant CT-scanner time and relatively high radiation dosage.

On-line visualization can include, for example, techniques that visualize the target lesion by inserting an ultrasound transducer through a working channel of the bronchoscope. There is no significant difference in sensitivity compared to unguided TBNA.

Tracking methods can include techniques that track the tip of the bronchoscope in real-time to guide the TBNA. For example, tracking the bronchoscope's tip by processing the endoscope images. The Biosense intra-body navigation system uses electromagnetic fields to track a sensor that can be attached to the bronchoscope's tip. In an in vivo study, ten to twenty markers were secured on a test subject's chest and the respiratory motion was monitored using a second sensor to compensate for breathing motion. The study showed an accuracy of 4.2 mm+−2.6 mm (+−SD).

However, no known system or method exists for guiding a flexible instrument using predetermined models. Therefore, a need exists for a method of blindly guiding a flexible instrument according to a predetermined patient specific model.

SUMMARY OF THE INVENTION

According to an embodiment of the present invention, a method is provided for determining instructions for handling a flexible instrument. The method comprises parameterizing the flexible instrument according to a plurality of parameters for handling the instrument, determining at least one instrument configuration, wherein the configuration describes at least one parameter, and determining instructions for handling the instrument according to the configuration.

Parameterizing further comprises determining an instrument length. Parameterizing further comprises determining a shaft rotation of the flexible instrument. Parameterizing further comprises determining an angle of deflection of a tip of the instrument. Parameterizing further comprises determining a tool length.

The configuration comprises a value for at least one parameter. The configuration describes at least one parameter that docks the flexible instrument with a target. One or more parameters of the configuration are determined relative to an anatomical landmark.

The method comprises determining a patient model.

According to an embodiment of the present invention, a method is provided for determining instructions for handling a flexible endoscope. The method comprises parameterizing the flexible endoscope according to a plurality of parameters for handling the endoscope given a desired task, and determining, pre-operatively, at least one endoscope configuration of the parameters, based on a predetermined patient model. The method further comprises determining instructions for handling the endoscope according to the configuration.

The method comprises determining a digital model of a flexible instrument.

The method comprises registering a patient to the predetermined patient model. The method comprises identifying a mutual landmark visible in the patient and in the predetermined patient model. The method comprises determining a configuration relative to a landmark. The landmark is a carina of a tracheobronchial tree.

Parameterizing further comprises determining an endoscope length parameter. The method comprises inserting the endoscope model to a landmark, and inserting the endoscope model to a target site, wherein a distance to the target site from the landmark is a difference between a total distance from a reference point to the target site and an intermediate distance from the reference point to the landmark.

Parameterizing further comprises the step of determining a shaft-rotation of the endoscope according to a landmark. The method comprises determining an angle between a bending plane of a tip of the endoscope model and the target.

Parameterizing further comprises the step of determining a bending angle of the endoscope. Determining the bending angle comprises approximating a bending movement by a semi-circle with a given center, determining a vector between the center and the tip of the endoscope model, determining a vector between the center and the target, determining the angle between both vectors.

Parameterizing further comprises the step of determining a tool length and more specific a distance between the tip of the instrument and the target. Determining the tool length comprises determining the distance between the aligned tip of the endoscope model and the target.

According to an embodiment of the present invention, a system is provided for monitoring the configuration of a flexible instrument. The system comprises an endoscope comprising a wheel and wheel angle-scale for determining a tip deflection of the endoscope, a stopper fixed to a shaft of the endoscope, a pointer fixed to the shaft of the endoscope, and a mouth-piece comprising an angle-scale, wherein the angle-scale is a reference point for the pointer for determining a shaft-rotation.

The stopper is fixed to a position on the shaft according to a distance from the mouth-piece to the target site. The shaft passes through the mouth-piece.

BRIEF DESCRIPTION OF THE DRAWINGS

Preferred embodiments of the present invention will be described below in more detail, with reference to the accompanying drawings:

FIG. 3 is an illustrative diagram of an endoscope and a patient according to an embodiment of the present invention;

FIG. 4 is an illustrative set of instructions according to an embodiment of the present invention;

DETAILED DESCRIPTION OF PREFERRED EMBODIMENTS

According to an embodiment of the present invention, an endoscopic procedure can be guided according to a predetermined method. The method of guiding the instrument can be based on a parameterization of the instrument and a plurality of instrument configurations determined to accomplish a goal. The method of guiding the instrument can be implemented with or without the aid of a computer. Thus, costs, including for example, setup time, associated with an intervention using a method according to the present invention can be substantially less than for procedures which implement computer technology in an operating theater.

Figure 1:
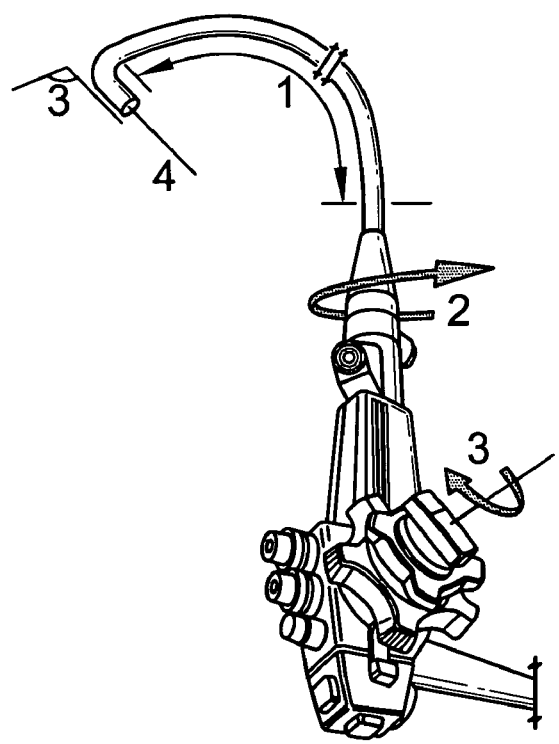
FIG. 1 is a diagram of an endoscope according to an embodiment of the present invention.

For example, a bronchoscope can be described relative to a landmark. Referring to FIG. 1, these parameters can include: Bronchoscope insertion depth l (1); shaft rotation about the principal axis $\alpha$ (2); an angle of tip detection $\beta$ controlled by an angling wheel (3); and a needle length d (4).

These parameters can be denoted as endoscope configuration C=(l, $\alpha$, $\beta$, d). An instrument can be described by one or more configurations. The configurations can be described as a method for performing a task, for example, a TBNA.

A method of guiding a flexible instrument according to the present invention can increase a probability of success for a TBNA by providing these parameters and detailed step-by-step instructions to a user, e.g., a surgeon. The instrument parameters and configurations can be determined prior to the intervention.

A patient specific model can be determined, for example, by a CT scan or an MRI. For example, the patient specific model can show a tracheobronchial tree derived from a CT scan. By registering the patient to the patient model, a task, e.g., biopsy, can be simulated by determining the possible endoscope configurations that reach the target site given the parameters of the instrument relative to the patient.

From the instrument configurations, one or more frequency distributions can be determined for each parameter. In the case of TBNA, to exploit the fact that several aspirations can be performed for one biopsy, several sets of the most frequent parameters can be selected from these distributions. During the intervention a method of guiding a flexible instrument can be used to monitor the parameters; the method is an example of a passive control. Thus, the aspirations can be performed systematically. The instrument's parameters can be determined relative to the patient's model or reference frame, which can be registered according to an anatomical landmark.

A model of the flexible instrument, e.g., bronchoscope, takes physical characteristics, including for example, flexibility, bending section, diameter and length of the bronchoscope into account. The bending section of the bronchoscope is its flexible distal end. It can be controlled using the angling wheel located at the bronchoscope's control head, to look around and guide the needle to the target.

Figure 2A:
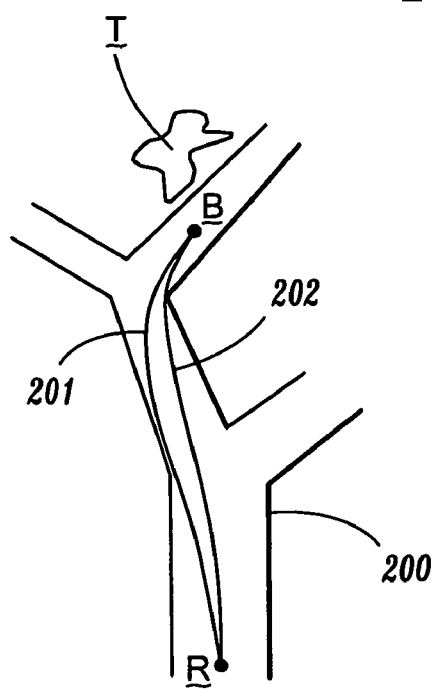
FIG. 2a is an illustrative diagram of a tracheobronchial tree and possible endoscope arragnements according to an embodiment of the present invention.

FIG. 2a shows an example of the components of a TBNA. It shows the tracheobronchial tree 200 and a target mass (T) outside the airways. The planned biopsy site B is shown in form of the endoscope's tip together with two possible shaft shapes. Note, that B is the position and orientation of the tip before the alignment and therefore does not need to point towards the target. The calculation of the protocol parameters l, $\alpha$, $\beta$, d can be based on a model M of the bronchoscope and comprises preoperatively planning biopsy site B, determining the bronchoscope length l to reach B: l=M(B), determining the endoscope-space E to reach B with length l: E=M(l,B), and for all e$\in$E: determining $\alpha$m(e), $\beta$=M(e), d=M(e).

The physician preoperatively plans a biopsy site. The biopsy site B represents roughly the position and orientation of the bronchoscope's tip within the tracheobronchial tree from where to perform the biopsy.

A TBNA procedure can be considered as a two step method: (1) inserting the bronchoscope into a branch that includes the target-site and (2) aligning the bronchoscope with the target lesion. This allows the method to fix the inserted length l and to determine the alignment parameters $\alpha$, $\beta$, d based on the fixed inserted length.

Instrument model M can be used to determine a set of instrument shapes or configurations where each element represents an instrument of length l that reaches into the branch including the target site B. This set of shapes can be referred to as the endoscope-space E, since it describes the possibilities of a real instrument, e.g., bronchoscope, to reach the target site.

Given the endoscope-space E, a method determines for each endoscope shape the alignment parameters α, β, d. For β and d, alignment parameters can be determined according to a bending section model.

To register the insertion depth l and shaft rotation α to the patient's reference frame, a landmark based method can be used. For example, the carina, a keel-shaped part of the tracheobronchial tree that marks the bifurcation of the trachea into the left and right lung, can be used as an anatomical landmark.

Figure 2B:
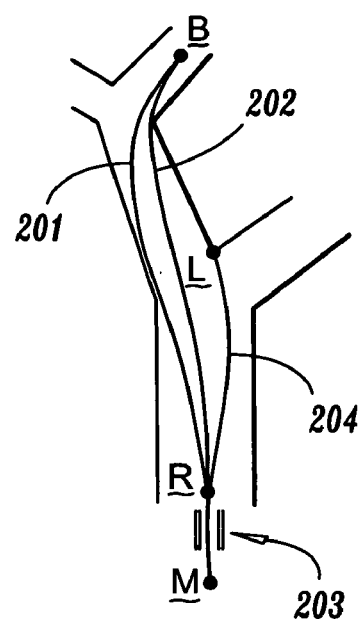
FIG. 2b is an illustrative diagram of a tracheobronchial tree and references according to an embodiment of the present invention.

FIGS. 2a and 2b show a biopsy-site B and two possible endoscope lengths 201–202 from B to the point of reference R. The point of reference can be chosen to lie in a bottleneck 203 (e.g., vocal chords) in terms of all possible paths the instrument can take. To determine the bronchoscope length to B measured from M, the physician can touch the landmark L with the bronchoscope 204 and insert (or withdraw for lesions proximal to the carina) the bronchoscope by the difference between RB and RL.

As the mutual zero-point for the shaft-rotation, the rotation of the bronchoscope that shows the carina to appear vertically can be selected. This rotation registers the patient to the patient's model, and can be the basis for the instrument parameters. In a planning phase the physician can rotate a virtual endoscopic camera and during the intervention rotate the bronchoscope until the views show the carina to appear vertically.

To set the bronchoscope to the configuration given by the instrument parameters, control over the inserted length l, the shaft rotation a, the tip detection β and needle length d is needed. Referring to FIG. 3, since the needle aspirations can be performed based on a fixed bronchoscope length, a stopper 301 can be used to prevent the bronchoscope 302 from penetrating the body deeper than desired. To control shaft rotation, a goniometer 303 (angle-scale) can be attached to the base plate 304 of the mouth-piece and a pointer 305 to the stopper 301. When the base plate 304 stops the insertion of the bronchoscope 302, shaft rotation moves the pointer 305 along the angle-scale 303. The tip bending can be controlled with an angle-scale attached to the angling wheel 306 located at the bronchoscope's control head.

During the planning phase, a look-up table can be used to map the angle of tip deflection to the wheel angle. A tool length, e.g., needle length, can be controlled according to marks on its proximal end and using the opening of the biopsy port as a reference point.

FIG. 4 shows a TBNA-protocol according to an embodiment of the present invention. It can be divided into three parts: Lines 1–5 comprise the registration instructions and lines 6–7 describe the insertion or withdrawal of the bronchoscope to the biopsy-site. Lines 8–10 describe the alignment of the bending section with the target lesion. Parameters l, a, β, d represent the patient specific part of the protocol. The instructions themselves can remain substantially unchanged for different patients. Depending on the location of B relative to the current endoscope position, the left or right column of lines 6–7 can be executed. After execution of line 7, the bronchoscope reached the biopsy-site and the following instructions 8–10 use parameters α, β, d to align the bronchoscope with the target lesion. The arrow indicates that a series of biopsies can be performed systematically.

Figure 5:
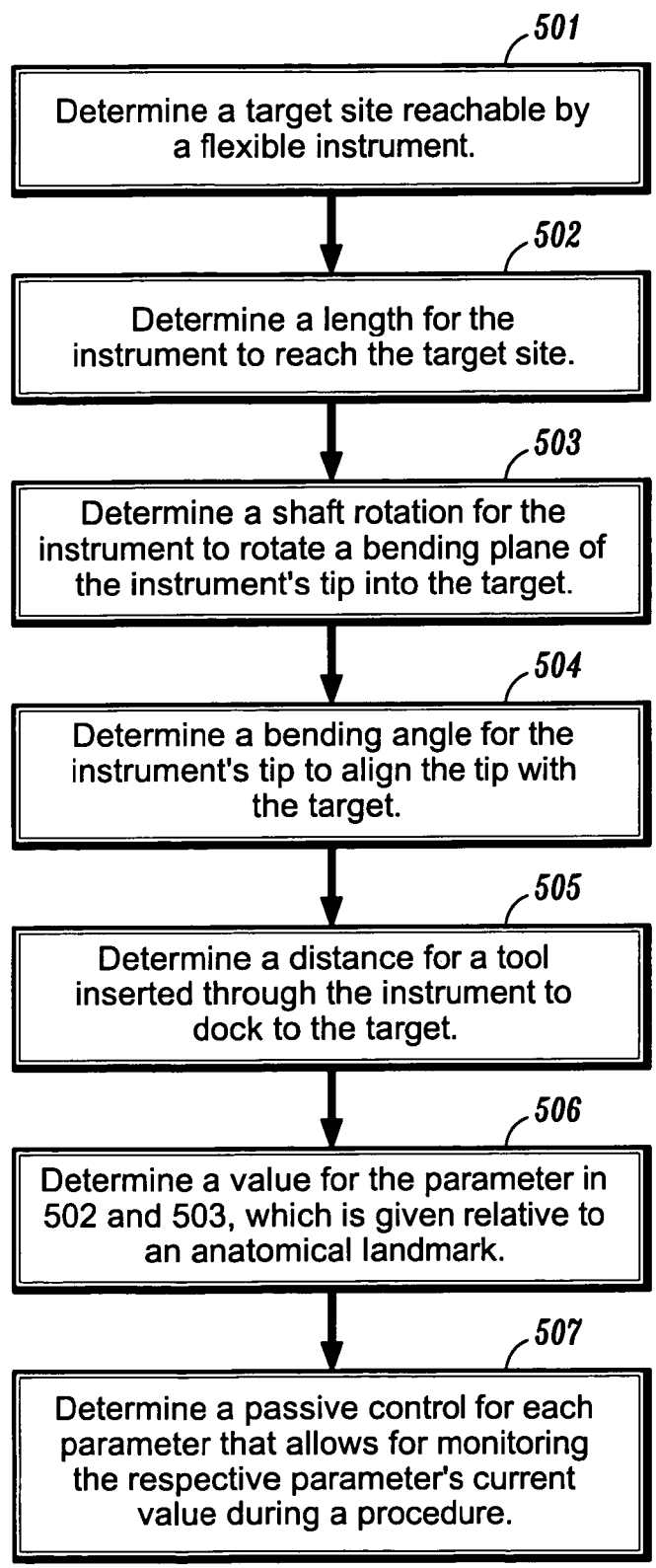
FIG. 5 is a flow chart of a method according to an embodiment of the present invention.

FIG. 5 shows a method for guiding a flexible instrument, e.g., an endoscope, to a target site. The method comprises determining the target site reachable by a flexible instrument 501, determining a length for the instrument to reach the target site 502, and determining a shaft rotation for the instrument to rotate a bending plane of the instrument's tip into the target 503. The method further comprises determining a bending angle for the instrument's tip to align the tip with the target 504, determining a distance for a tool inserted through the instrument to dock to the target 505, and determining a value for the parameter in 502 and 503, which is given relative to an anatomical landmark 506. The method comprises determining a passive control for each parameter in 502, 503, 504 and 505 that allows for the monitoring of the respective parameter's current value during the procedure 507.

The instrument model M describes a flexible endoscope as a chain of rigid cylinders interconnected by discrete ball-and-socket joints. The chain interacts with the patient specific anatomical model via a collision detection method. Each cylinder of the chain can be approximated by a cloud of sample points on its surface. Checking for collision of all sample points with the organ model allows us to verify whether a chain configuration represents a valid endoscope shape. The flexibility of the chain can be modeled by the choice of link length s (span) and joint range θ and is based on the notion of minimal radius. Thus, a method can exhaustively enumerate all possible chain configurations, given a start cylinder and a plurality of constraints. These constraints can include, for example, organ geometry, gravity, medial-axis and stopping-criteria. Using a recursive backtracking method, a tree data structure can be created where the nodes represent joints of the chain. The bending section (e.g., 95 mm long) can be modeled accurately to reflect the properties of a real bronchoscope.

A link can be represented by a reference frame (4×4 homogeneous transform matrix) L, where the centerline of the cylinder is the z-axis of the frame and the cylinder bases lie in the z=0 and z=s plane. Given a link $L_i$ of level i, the nine connected links of the next level can be given by:

$$L_{i+1}^j = R(r_j, \theta) L_i T(\hat{z}s), \text{ for } j=1, 9,$$

where T is a translation and R a rotation matrix, $\hat{x}, \hat{y}, \hat{z}$ denote the three 4×1 unit vectors, $r_j$ is the jth rotation vector of the set $\{(xy0)^T | x, y \in \{-1, 0, 1\}\}$ and θ is the rotation angle.

For determining the length of the endoscope needed to reach a target link (e.g., biopsy-site), the stopping criteria can be determined to be fulfilled when a link L docks to the target link. For determining the endoscope-space E the stopping criteria can be the recursion depth.

For each path from the root to a leaf, alignment parameters can be determined. The shaft rotation α is dependant on the orientation of the bronchoscope's bending plane. The bending plane of an endoscope is the plane in which the tip moves under the rotation of the bending wheel at the endoscope's control head. Let tip link L and target vector t be known with respect to the same global reference frame and let L's y=0-plane be the bending plane. The desired shaft rotation is the rotation angle about $\hat{z}$ that rotates the y=0-plane into target t:

$$\alpha = \cos^{-1}\left(\frac{t' \cdot \hat{x}}{|t'||\hat{x}|}\right) \text{ with } t' = (L^{-1}t)(1101).$$

The left-hand-side of the formula calculates the angle between unit vector $\hat{x}$ and t'. Vector t' equals t known with respect to L and orthogonally projected into the z=0-plane.

Figure 6:
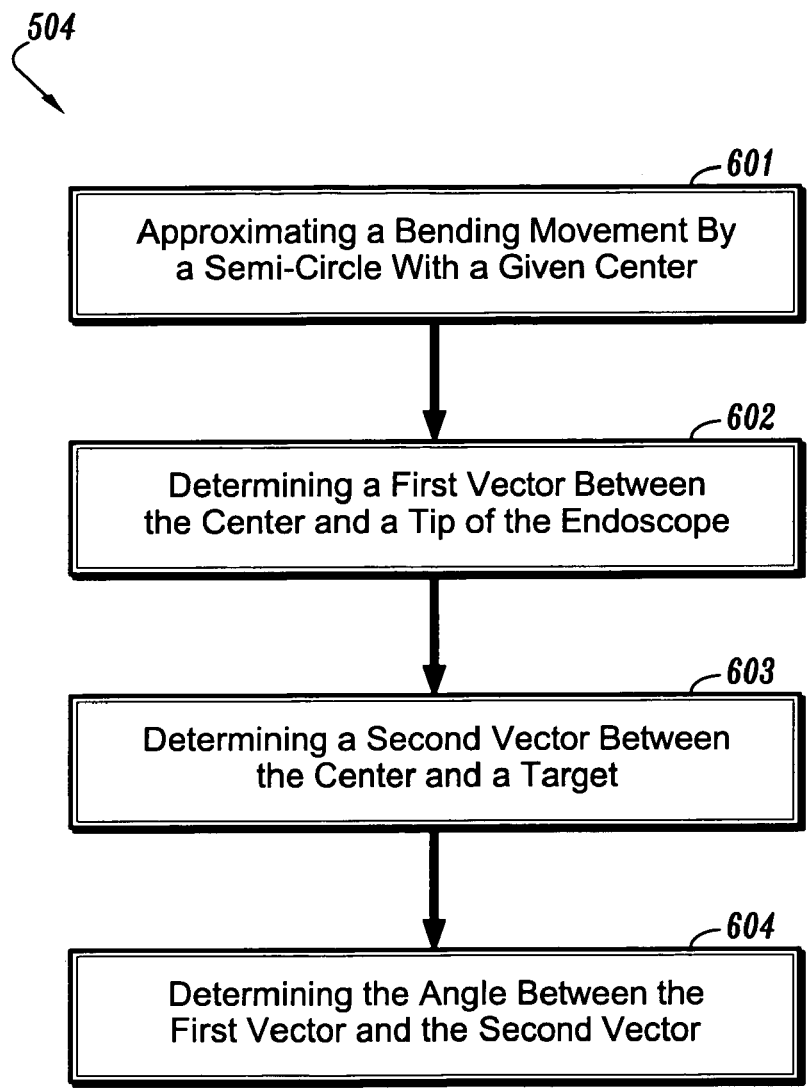
FIG. 6 is a flow chart of a method according to box 504 of FIG. 5.

After shaft rotation, target t lies in the y=0 bending plane and the method determines the angle of bending wheel rotation needed to align the tip with t. The transition point q from the shaft to the bending section determines the angle of wheel rotation. As shown in FIG. 6, the bending movement of the straight tip to the left and right can be approximated by a semi-circle with its center c =49 mm away from the endoscopes end 601. A link Q of the chain can be determined that includes q. The link can be moved along its ẑ-axis by a =95 −49 =46 mm. The new origin of Q can be considered as the center of the semicircle. The desired angle of wheel rotation (604) can be given by the angle between ẑ (602) and target t (603):

$$\beta = \cos^{-1}\left(\frac{Q'^{-1}t \cdot \hat{z}}{|Q'^{-1}t||\hat{z}|}\right) \text{ with } Q' = QT(\hat{z}a). \text{ Needle length } d = |Q'^{-1}t| - c.$$

This approach has been implemented on a SGI PC540, 550 Mhz (single), 0.5 GB RAM, running Windows 2000 and OpenGL. A lung phantom was built using transparent (for visual verification) PVC cylinders. Thirty-seven marker sticks (4 mm diameter, cardboard) were randomly placed in the model so that they are aligned with the inner surface of the cylinders. The phantom was then scanned (512×512× 382, 1 mm slice distance, 1.2 thickness). After the scan, the surface points were manually identified as target points. The lung phantom is 1.5 times the size (trachea diameter: 30 mm) of an adult lung, to compensate for the fact that a "Gastrointestinal Videoscope" (Olympus GIF 100, shaft diameter: 9.5 mm) was used for the experiments, the Videoscope being about 1.5 times the diameter of an endoscope.

Out of all 37 markers five were selected as target points, three of them close to the carina. For each target, the protocol was executed 20 times and record the configuration parameters needed to touch the marker stick with the biopsy needle. Note, that the markers can be seen by the endoscopic video camera as a white 4 mm disk. To estimate the parameters for each target, a method generates for each parameter a dataset of at least 100 (and up to 25,000) measures. Each dataset can be read with a data-analyzing package (IDL, Research System, Inc.) and create frequency distributions to draw histograms and calculate the mean and standard deviations.

Repeatability: To calculate the variation of the experimentally obtained parameters, the smallest and largest outlier of all 15 datasets (20 measures each) were rejected and the range of each dataset was determined. The largest range of α, β and d were determined to be 7°, 6° and 7 mm and the average range to be 6°, 4° and 4 mm respectively.

Accuracy of the prediction: The real error of a configuration C=(α, β, d) is given by the distance between the target point and the needle tip after setting the endoscope to configuration C. Since it may not be possible to measure distances inside the plastic model, a theoretical error model was used to obtain an upper bound error estimation for the parameter prediction. Results show, that shaft rotation α is by far the most sensitive parameter with an average error of 12°, whereas β (3°) and d (1 mm) can be predicted more accurately. To exploit this fact, a test was performed where the configuration ($\bar{\alpha}$, $\bar{\beta}$, $\bar{d}$) was taken for the first aspiration, ($\bar{\alpha}+\sigma$, $\bar{\beta}$, $\bar{d}$) for the second and ($\bar{\alpha}-\sigma$, $\bar{\beta}$, $\bar{d}$) for the third, where the dashed parameter denotes the mean and o the standard deviation of the respective distribution. The test shows that we could hit in worst-case targets of 24 mm diameter with one aspiration and 12 mm targets with three aspirations.

On average 13 mm targets can be hit with one aspiration and 5 mm targets with three aspirations.

According to an embodiment of the present invention, a method for guiding blind biopsies includes preoperatively calculating parameter sets that describe how to handle the bronchoscope to maximize the success probability. During the intervention, the surgeon follows step-by-step instructions (protocol), which are based on the parameter sets, to perform a series of systematic needle aspirations. An important feature of this approach is its simplicity. A method according to the present invention does not need additional devices or computers that need to be calibrated or operated in the operating room. The method controls are passive, intuitive to operate and remain outside the body. After the intervention the controls can be easily removed and the bronchoscope can be sterilized as usual. A method according to the present invention can be real-time during the intervention, in contrast to some image based approaches. The surgeon operates at his/her own speed. Off-the-shelf bronchoscopes (fiber optic or video) are applicable to the present invention, as well as any other flexible device such as a catheter. Registration of a method can be based on one or more anatomical landmarks.

Results with a lung phantom show that the repeatability is high enough to expect a maximum accuracy of 5 mm. Tests show that we are able to hit in worst-case targets of=12 mm diameter (average-case: 5 mm) with three aspirations.

Having described embodiments for a method of guiding a flexible cylinder, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A method for handling a flexible endoscope comprising the steps of:
   parameterizing the flexible endoscope according to a plurality of parameters for handling the endoscope given a desired task;
   determining, pre-operatively, at least one endoscope configuration of the parameters, based on a predetermined patient model;
   determining instructions for handling the endoscope according to the configuration;
   handling the endoscope according to the instructions.

2. The method of claim 1, further comprising determining a digital model of a flexible endoscope.

3. The method of claim 1, further comprising the step of registering a patient to the predetermined patient model.

4. The method of claim 1, further comprising the step of identifying a mutual landmark visible in a patient and in the predetermined patient model.

5. The method of claim 4, wherein the landmark is a carina of a tracheobronchial tree.

6. The method of claim 1, further comprising the step of determining a configuration relative to a landmark.

7. The method of claim 1, wherein the step of parameterizing further comprises determining an endoscope length parameter.

8. The method of claim 7, further comprising the steps of:
inserting the endoscope to a landmark; and
inserting the endoscope to a target site, wherein a distance to the target site from the landmark is a difference between a total distance from a reference point to the target site and an intermediate distance from the reference point to the landmark.

9. The method of claim 1, wherein the step of parameterizing further comprises the step of determining a shaft-rotation of the endoscope according to a landmark.

10. The method of claim 9, wherein determining a shaft-rotation comprises determining an angle between a bending plane of a tip of the endoscope and a target.

11. The method of claim 1, wherein the step of parameterizing further comprises the step of determining a bending angle of the endoscope.

12. The method of claim 11, wherein determining the bending angle comprises the steps of:
approximating a bending movement by a semi-circle with a given center;
determining a first vector between the center and a tip of the endoscope;
determining a second vector between the center and a target; and
determining the angle between the first vector and the second vector.

13. The method of claim 1, wherein parameterizing further comprises the steps of:
determining a tool length, wherein the tool is coupled to a tip of the endoscope; and
determining a distance between the tip of the endoscope and a target.

14. The method of claim 13, wherein determining the tool length comprises determining the distance between an aligned tip of the endoscope and a target.

15. The method of claim 1, wherein determining instructions for handling the endoscope according to the configuration are determined prior to inserting the flexible endoscope into a patient.

* * * * *